United States Patent [19]

Yemoto et al.

[11] Patent Number: 4,524,018

[45] Date of Patent: Jun. 18, 1985

[54] LASTING FRAGRANT ARTICLE USING GRADUALLY DECOMPOSING PERFUME

[75] Inventors: Jiichiro Yemoto, Kumamoto; Ryokichi Tarao, Kanagawa; Yoshio Yamamoto, Kumamoto, all of Japan

[73] Assignees: Chisso Corporation, Osaka; S.T. Chemical Co., Ltd., Tokyo, both of Japan

[21] Appl. No.: 402,810

[22] Filed: Jul. 28, 1982

[30] Foreign Application Priority Data

May 28, 1982 [JP] Japan .................... 57-90946

[51] Int. Cl.³ .................... A61K 7/46; C11B 9/00
[52] U.S. Cl. .................... 252/522 A; 428/905
[58] Field of Search .................... 252/522 A; 428/905

[56] References Cited

U.S. PATENT DOCUMENTS 3,215,719 11/1965 Allen et al. .................... 252/522 X
4,169,069 9/1979 Unger et al. .................... 252/522 X

OTHER PUBLICATIONS

Chemical Abstracts 92 203382y (1980).

*Primary Examiner*—Helen M. S. Sneed
*Attorney, Agent, or Firm*—Wenderoth, Lind & Ponack

[57] ABSTRACT

Lasting fragrant article formed by impregnating a pregnant with a composition prepared by compounding a single perfume or blend of perfumes with a compound represented by the general formula:

$$R_a Si(OR')_b (OR'')_c$$

wherein R, R', and R'' represent hydrocarbon residues and R'' represents a group which develops aroma in the form of R''OH; $a+b+c=4$; and $c \geq 1$; or its product formed by hydrolysis or dehydration condensation. The fragrant article is characterized by the use of particular compounds, resulting in persistent aroma, and it is subject to very little change in the fragrance tone.

5 Claims, 1 Drawing Figure

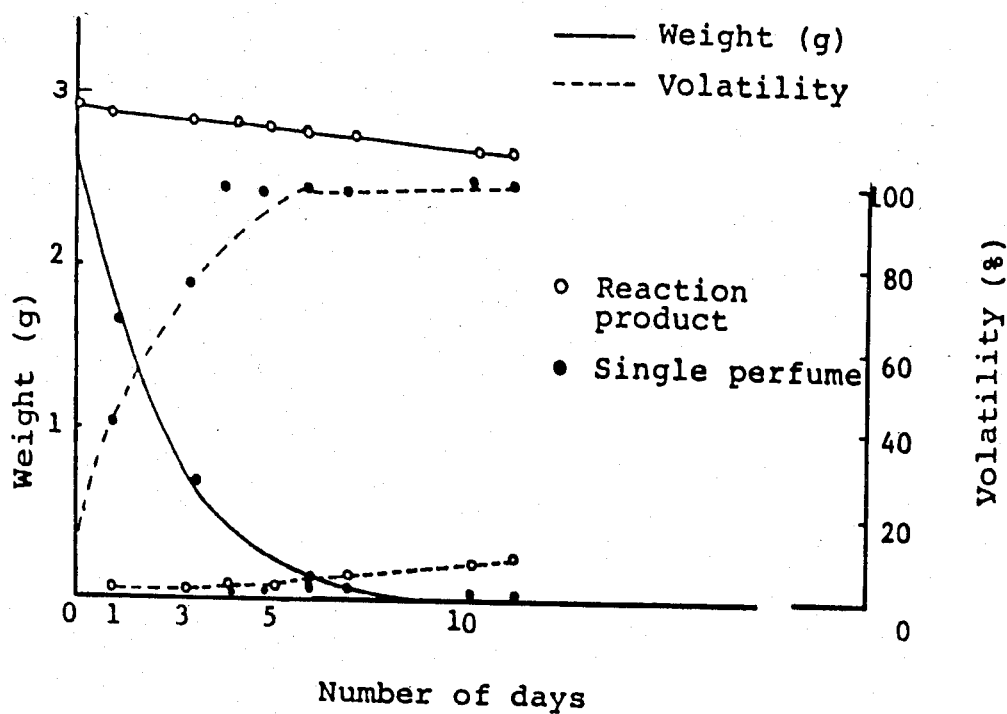

LASTING FRAGRANT ARTICLE USING GRADUALLY DECOMPOSING PERFUME

BACKGROUND OF THE INVENTION (1) Field of the Invention

This invention relates to a fragrant article using gradually decomposing perfume.

(2) Description of the Prior Art

There have hitherto been such impregnation type fragrant articles as formed by adding a perfume to a sublimable substance such as para-dichlorobenzene, etc. or to crystalline cellulose, etc. as an excipient. However, all of these fragrant articles have only a small amount of perfume added thereto. Under the circumstances, they have drawbacks such as a short duration of volatilizing the aroma, and weak aroma.

There have been recently available improved plastic fragrant articles formed by compounding a perfume in a plastic such as vinyl chloride, etc. There is however required a high temperature for mixing plastics with perfume, because they are, in general, poorly compatible with each other. This makes it unfavorable to use a volatile perfume, resulting in that choice of the variety of perfumes is naturally limited. There is also a drawback in that although the aroma is strong enough in the initial stage of use, the intensity of the aroma notably decreases in a few days.

There have also been marketed several types of fragrant articles wherein a perfume is added to impart aromaticity to a pregnant, such as filter paper, chipboard used as building material, zeolite, silica gel or the like. The perfume for this purpose is rarely used in a singular form, and there are used several blend perfumes arranged by mixing various kinds of single perfumes, which have strong aroma. Since, in this case, the volatilization rates of the respective perfume components differ from one another, the composition of the perfume changes with the lapse of time, resulting in change of the fragrance tone. In order to resolve this problem, there are often added, as a retainer, balsam, benzoin, musk, glycols, or phthalates, as they have low volatility, strong affinity and high retainability. However, these types of retainers not only supress the volatilization rates of these components having high volatilization rates, but also supress the volatilization rates of those components of low volatilization rates. As a result, the aroma tends to be weak.

SUMMARY OF THE INVENTION

The object of this invention is to provide a fragrant article which has persistent aromaticity and which is subject to very little change in fragrance tone.

The subject matter of this invention resides in a fragrant article characterized by impregnating a pregnant (substrate to be impregnated) with a composition prepared by compounding a single perfume or blend of perfumes with one or more aromatizing components selected from the compounds represented by the general formulae:

$$R_a Si(OR')_b (OR'')_c \quad \text{(I)}$$

and

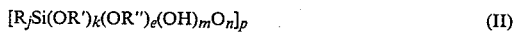

$$[R_j Si(OR')_k (OR'')_e (OH)_m O_n]_p \quad \text{(II)}$$

wherein R is selected from the group consisting of a saturated or an unsaturated aliphatic hydrocarbon group, an aromatic hydrocarbon group, an aliphatic hydrocarbon substituted aromatic hydrocarbon group, an aromatic hydrocarbon substituted aliphatic hydrocarbon group, the hydrocarbon groups having 1 to 10 carbon atoms, and hydrogen; R' represents an alkyl or alkenyl group having 1 to 5 carbon atoms; R'' is selected from the group consisting of a saturated or an unsaturated aliphatic hydrocarbon group, an aromatic hydrocarbon group, an aliphatic hydrocarbon substituted aromatic hydrocarbon group, and an aromatic hydrocarbon substituted aliphatic hydrocarbon group, the hydrocarbon groups having 4–15 carbon atoms, with the proviso that R'' develops aroma in the form of R''OH; each of R, R', and R'' may be the same or different if two or more of them are present in the same molecule; a is zero or an integer of from 1 to 3, b is zero or an integer from 1 to 3, c is an integer of from 1 to 4, provided that $a+b+c=4$; j and m are each a numeral from zero to 3 inclusive; $0 \leq k < 4$; $0 < e < 4$; $0 \leq n < 2$; $j+k+e+m+2n=4$, and p is a positive integer.

BRIEF DESCRIPTION OF THE DRAWING

FIG. 1 shows the respective volatilization states of the gradually decomposing perfume in the present invention and that of the conventional single perfume.

DETAILED DESCRIPTION OF THE INVENTION AND THE PREFERRED EMBODIMENTS

In the abovementioned general formula (I) and formula (II), illustrative of R are a saturated or unsaturated or aromatic hydrocarbon group, such as methyl, ethyl, propyl, vinyl, allyl, phenyl, etc.

Referring to these groups, it is preferable to use the groups having 1 to 4 carbon atoms, such as alkyl and alkenyl, because the compounds having such groups exhibit a rapid formation reaction of (I) or (II), and their sources are easily available.

R'' is a group that is slowly released in a form of R''OH from the compound (I) or (II) by hydrolysis and volatilizes into the atmosphere, whereby aroma can be sensed by man. R' is a group that remains, for example, when an alcohol substitution is conducted by causing reaction between an organic silicon compound represented by reactant material $R_x Si(OR')_{4-x}$ (where x is 0, 1, 2, or 3) of the compound (I) with an alcohol compound that develops aroma in a form of R''OH, and is present in compound (I).

Examples of alcohols represented by R'OH, to which R' corresponds, include methanol, ethanol, n-propanol, iso-propanol, n-butanol, iso-butanol, sec-butanol, and pentanol (n-pentanol, methylbutanol, etc.). It is preferable to use the compounds having the group R' of 1 to 3 carbon atoms, because of rapid formation reaction in the compound (I) or (II) and ease of obtaining them.

Examples of alcohols represented by R''OH, to which R'' corresponds, include saturated aliphatic alcohols such as n-butanol, iso-butanol, sec-butanol, pentanol (n-pentanol, methyl butanol, etc.), hexanol (n-hexanol, methyl pentanol, ethyl butanol, etc.) and the like, unsaturated aliphatic alcohols, such as prenol, cis-3-hexanol, trans-2-hexenol, sorbyl alcohol, cis-4-heptenol, trans-2-octenol, trans-4-decenol, trans-2-cis-6-nonadienol, geraniol, citronerol, nerol, etc., aliphatic hydrocarbon substituted phenol, such as eugenol, vanillin, 4-(p-hydroxyphenyl)-2-butanon, etc. and aromatic hydrocarbon substituted aliphatic alcohols, such as β-phenylethylalcohol, cinnamic alcohol, benzyl alcohol, etc.

Referring to these types of alcohols, alcohols having 8 or less carbon atoms, such as trans-2-octenol, cis-3-hexenol, pulenol, etc. are fragrant components which are referred to as the so-called "top note" type. Although they give a refreshing aroma as a blend perfume component, they have a problem in that they are very volatile and are lost in a short period of time, and are especially susceptible to imbalance of the blend perfume. This problem can be resolved by using the composition of this invention in place of these components.

The alcohols having 4 or 5 carbon atoms such as n-butanol, pentanol, etc. are mentioned as both examples of R'OH and R"OH, and can be used in either case. Namely, they can be introduced into the compound (I) or (II) as a perfume component R"O, or they can be introduced as R'O directly from the starting material compound $R_xSi(OR')_{4-x}$ into the compound (I) or (II), though they are not the desired perfume components.

Specific examples of the compounds represented by the general formula (I) are:

$$CH_2=CHSi(OC_2H_5)_b(OC_6H_{11})_c$$

corresponding to cis-3-hexenol (molecular formula: $C_6H_{11}OH$);

$$CH_3Si(OCH_3)_b(OC_{10}H_{17})_c$$

corresponding to geraniol (molecular formula: $C_{10}H_{17}OH$);

$$CH_3Si(OC_2H_5)_b(OC_6H_{11})_c$$

corresponding to trans-2-hexenol (molecular formula: $C_6H_{11}OH$); and $$CH_3Si(OC_2H_5)_b(OC_8H_9)_c$$

corresponding to 2-phenylethylalcohol (molecular formula: $C_8H_9OH$), etc.

As a method of producing the compound represented by the general formula (I), it is possible to utilize, for example, the reaction between the aforementioned R'OH or R"OH alcohol compound with a silicon compound having silicon-halogen bonding and/or silicon-acyloxy bonding, such as methyl trichlorosilane and vinyl acetoxysilane, etc. The reaction can be carried out at an ambient temperature or at an elevated temperature, for example, under atmospheric pressure without using a catalyst or using a catalyst, such as an amine compound and a pyridine compound. When importance is attached to the absence of the remaining catalyst in the reaction product, it is preferably to conduct this reaction without using a catalyst. Refer to, as synthesis method, Indian J. Chem. Vol. 12, October 1974, pp. 1099–1101 and Vol. 13, December 1975, pp. 1364–1365.

As an alternative method of producing the compound represented by the general formula (I), it is possible to utilize such reaction as substituting the —OR" radical with part or all of the —OR' group of an organic silicon compound represented, for example, by the general formula $R_xSi(OR')_{4-x}$ through reaction between this organic silicon compound with an R"OH alcohol. The reaction can be conducted at an ambient temperature, but is preferably conducted at an elevated temperature. The catalyst to be used can be titanium alkoxide, octyl stannate, potassium carbonate, methyl trichlorosilane, p-toluenesulfonic acid, sodium, etc. If it is not desired that a catalyst remain in the reaction product, the reaction can be conducted without using the catalyst. In the reaction process, it is preferable to include with an additional step of removing R'OH produced by the substitution reaction from the reaction system, for example, by means of reflux.

It is believed that production of the compound represented by the general formula (I) is accompanied by production of a plurality of types of compounds.

The compound represented by the general formula (II) is a compound that can be formed by a partial hydrolysis of the compound represented by the aforementioned general formula (I); or a compound that can be formed by condensation of the compound which can be produced by such partial hydrolysis.

The former compound that can be formed by the partial hydrolysis can be produced by adding water to the compound represented by the general formula (I), and preferably by heating this compound, followed by removing R'OH and/or R"OH produced by hydrolysis from the reaction system, for example, through distillation, if necessary.

The latter compound that can be formed by the aforementioned condensation can be obtained by condensing the compound that can be formed by the aforementioned partial hydrolysis using acid or alkali as a catalyst or without using the same. Refer to "Organo-silicon Compounds" 1, published by Academic Press, 1965, p. 41, for example.

There may be mentioned as examples of pregnants used in the present invention, glass fiber, a bundle of asbestos, a bundle of fine glass tubes, aluminum foil bent zigzag and piled on or joined to another aluminum foil or the like; woven fabric, nonwoven fabric, knitted goods and felt-like material made of metal, asbestos, rock wool, cellulose, wool or synthetic fiber; Japanese paper, tissue paper, corrugated cardboard; continuously or discontinuously foamed material; and aggregated beads, sinter, unglazed chinaware, vermiculite, and zeolite. The surface of these materials can be impregnated with a blend perfume by partially covering it, for example, with film or foil having small permeability of gas and/or moisture.

The following methods can be used to impregnate the blend perfume (including the compound (I) or (II) in this invention) into the aforementioned pregnant. They are a method of immersing the impregnant in a liquid or solution of the blend perfume, and a method of impregnating a liquid or solution of the blend perfume into the pregnant through contact by dropping, pouring, or spraying the former onto the latter.

The gradually decomposing perfume used in the present invention is slowly liberated and diffuses its original perfume components through decomposition by moisture in air, so that the continuity of aroma is considerably prolonged. Besides, this perfume has advantages in that it has excellent compatibility with the conventional perfumes, and its various properties such as stability are hardly impaired when blended, permitting blending with any other perfume at will. Furthermore, unlike the conventional blend perfume whose fragrant tone changes in a short period of time, the blend perfume of the present invention is subject to very little change in the fragrance tone and can maintain its initial aroma for a long time.

The invention will become more clear when considered together with the following reference example and EXAMPLES which are set forth as being merely illustrative of the invention, and which are not intended in any manner to be limitative thereof. Unless otherwise indicated, all parts and percentages are by weight.

REFERENCE EXAMPLE

A comparison of the volatilization factor was made between a reaction product formed by reacting trans-2-hexenol, which is a single perfume frequently used in mixing green apple type perfume, with methyl triethoxysilane in a molar ratio of 2:1 and the single perfume (trans-2-hexenol alone). The pregnant used was square filter paper (No. 5300, made by Azumi Filter Paper Co., Ltd. in Japan) whose length is 50 mm and whose thickness is 2.75 mm. Two sheets of the filter paper were impregnated with 2.9 g of each of the aforementioned reaction product and the single perfume, in order to obtain fragrant articles, followed by volatilizing the impregnated articles at an average room temperature of 20° C. and an average relative humidity of 71 percent. FIG. 1 shows the result. As shown in the figure, there is a distinct difference in volatility between both articles.

EXAMPLE 1

0.4 Percent of a reaction product formed by reacting a single perfume (trans-2-hexenol) with methyl triethoxysilane in a molar ratio of 2:1, which was used in the foregoing Reference Example, and 0.9 percent of a reaction product formed from cis-3-hexenol and methyl triethoxysilane in a molar ratio of 2:1, were mixed with 98.7 percent of another perfume component to prepare a green apple type blend perfume. A fragrant article was prepared by impregnating the blend perfume into circular filter paper of 65 mm in diameter and 3 mm in thickness. The article was then volatilized at room temperature.

Evaluation was made in an odorless room (2 m³ space), with reference to the intensity of aroma and change of the fragrance tone due to the lapse of time.

For comparison, examination was made on a control article which was prepared by using a blend perfume of 0.4 percent and 0.9 percent of each single perfume, i.e. trans-2-hexenol and cis-3-hexenol, the blend perfume being a mixture of the respective perfumes before reaction, in place of the reaction product formed in a molar ratio of 2:1 with methyl triethoxysilane.

Table 1 shows the result. In this table, the numerals and symbols denote the following (the same applies to the succeeding tables).

| Aroma intensity | Change in fragrance tone |
| --- | --- |
| +3 Very strong | o No change |
| +2 Strong | ∆ Slight change |
| +1 Slightly strong | x Distinct change |
| 0 Not strong or weak | |
| −1 Slightly weak | |
| −2 Weak | |
| −3 Very weak | |

TABLE 1

| | Fragrant article of the invention | | Control article | |
| --- | --- | --- | --- | --- |
| | Strength | Tone of aroma | Strength | Tone of aroma |
| 1st day | +1~+2 | o | +2 | o |
| 5th day | 0 | o | 0 | ∆ |
| 10th day | 0 | o | −1 | x |
| 15th day | 0 | o | −1 | x |
| 21st day | 0 | o | −2 | x |
| 30th day | −1 | ∆ | −3 | x |

As can be seen from Table 1, the fragrant article of the present invention shows a very small change in the strength of aroma and almost no change in the fragrance tone, as compared with the control article.

EXAMPLE 2

As in the same manner of Example 1, a rose type blend perfume was arranged by mixing 35 percent, 10 percent, 0.5 percent, and 0.5 percent of the respective reaction products which were formed by reacting β-phenylethylalcohol, geraniol, cis-3-hexenol, and trans-2-hexenol with methyl triethoxysilane in a molar ratio 2:1, with 54 percent of another perfume component. Evaluation was then made on the intensity of aroma and change in the fragrance tone in accordance with the lapse of time in the same manner as in Example 1.

For comparison, a control article was prepared by using mixtures of 35 percent, 10 percent, 0.5 percent, and 0.5 percent of each single perfume before reaction, in place of the reaction products formed with methyl triethoxysilane in a molar raio of 2:1. The results are shown in Table 2.

TABLE 2

| | Fragrant article of the invention | | Control article | |
| --- | --- | --- | --- | --- |
| | Strength | Tone of aroma | Strength | Tone of aroma |
| 1st day | +2 | o | +3 | o |
| 5th day | +1 | o | +2 | o |
| 10th day | +1 | o | +1 | ∆ |
| 15th day | +1 | o | 0 | x |
| 21st day | 0 | o | −1 | x |
| 30th day | 0 | o | −2 | x |

As can be seen from Table 2, the fragrant article of the present invention shows very little change in the strength of aroma and almost no change in the fragrance tone, as compared with the control article.

EXAMPLE 3

As in Example 1, a floral green type blend perfume was arranged by mixing 1 percent, 10 percent, and 3.9 percent of reaction products formed by reacting trans-2-hexenol, geraniol, and β-phenylethylalcohol with methyl triethoxysilane in a molar ratio of 2:1, with 85.1 percent of another perfume component. Evaluation was made on the strength of aroma and change in the fragrance tone in accordance with the lapse of time in the same manner as in Example 1.

A control article was prepared by using a mixture of 1 percent, 10 percent, and 3.9 percent of each single perfume before reaction in place of the reaction products formed with methyl triethoxysilane in a molar ratio of 2:1. The results are shown in Table 3.

TABLE 3

|  | Fragrant article of the invention | | Control article | |
| --- | --- | --- | --- | --- |
|  | Strength | Tone of aroma | Strength | Tone of aroma |
| 1st day | +2 | o | +3 | o |
| 5th day | +1 | o | +2 | Δ |
| 10th day | +1 | o | +1 | x |
| 15th day | +1 | o | 0 | x |
| 21st day | 0 | o | −1 | x |
| 30th day | 0 | o | −2 | x |

As can be seen from Table 3, the fragrant article of the present invention shows very little change in the strength of aroma and almost no change in the fragrance tone, as compared with the control article.

What is claimed is:

1. A fragrant article which comprises a pregnant impregnated with a composition containing at least one perfume and at least one aromatizing component of the formula:

$$R_a Si(OR')_b (OR'')_c$$

wherein R is selected from the group consisting of hydrogen and a saturated or unsaturated aliphatic hydrocarbon group having 1 to 10 carbon atoms; R' is selected from the group consisting of alkyl and alkenyl having 1 to 5 carbon atoms; R'' is a saturated or an unsaturated aliphatic hydrocarbon group, having 5 or 6 carbon atoms, with the proviso that R'' develops aroma in the form of R''OH; each of R, R' and R'' may be the same or different if two or more of them are present in the same molecule; a is zero or an integer of from 1 to 3, b is zero or an integer of from 1 to 3, and c is an integer of from 1 to 4, with the proviso that $a+b+c=4$.

2. The fragrant article of claim 1 wherein R' is an alkyl or alkenyl group having 1 to 3 carbon atoms.

3. The fragrant article of claim 1 wherein R is an alkyl or alkenyl group having 1 to 4 carbon atoms.

4. The fragrant article of claim 1, wherein R'' is selected, in the form of R''OH, from the group consisting of pentanol, hexanol, prenol, cis-3-hexenol, trans-2-hexenol and sorbyl alcohol.

5. The fragrant article of claim 1, wherein R is methyl; R'' is ethyl; R'' is, in the form of R''OH, cis-3-hexenol or trans-2-hexenol; a is 1; b is zero or an integer of from 1 to 2; and c is an integer of from 1 to 3.

* * * * *